US006383131B1

(12) United States Patent
Yamamoto et al.

(10) Patent No.: US 6,383,131 B1
(45) Date of Patent: May 7, 2002

(54) STEREOSCOPIC ENDOSCOPE

(75) Inventors: Chikara Yamamoto; Hitoshi Miyano, both of Omiya (JP)

(73) Assignee: Fuji Photo Optical., Ltd., Saitama (JP)

( * ) Notice: Subject to any disclaimer, the term of this patent is extended or adjusted under 35 U.S.C. 154(b) by 0 days.

(21) Appl. No.: 09/566,264

(22) Filed: Sep. 17, 1999

Related U.S. Application Data

(63) Continuation of application No. 09/066,054, filed on Apr. 7, 1998, now Pat. No. 5,971,915.

(30) Foreign Application Priority Data

Jun. 13, 1997 (JP) .............................. 9-172863

(51) Int. Cl.$^7$ .............................................. A61B 1/05
(52) U.S. Cl. ..................................... 600/111; 600/166
(58) Field of Search ................................ 600/111, 129, 600/130, 161, 163, 166, 167, 176; 359/377, 462, 473, 45

(56) References Cited

U.S. PATENT DOCUMENTS

| 3,405,990 A | * | 10/1968 | Nothnagle | 359/376 |
| 4,824,228 A | * | 4/1989 | Wickholm | 359/462 |
| 4,916,534 A | * | 4/1990 | Takahashi | 600/175 |
| 5,522,789 A | * | 6/1996 | Takahashi | 600/111 |
| 5,547,457 A | * | 8/1996 | Tsuyuki | 600/173 |
| 5,588,948 A | * | 12/1996 | Takahashi | 600/173 |
| 5,649,897 A | * | 7/1997 | Nakamura | 600/111 |
| 5,689,365 A | * | 11/1997 | Takahashi | 600/111 |
| 5,743,846 A | * | 4/1998 | Takahashi | 600/111 |

FOREIGN PATENT DOCUMENTS

| JP | 8-122665 | 5/1996 | ........... G02B/23/26 |

* cited by examiner

Primary Examiner—John P. Leubecker
(74) Attorney, Agent, or Firm—Ronald R. Snider; Snider & Associates

(57) ABSTRACT

In an objective optical system of a stereoscopic endoscope, a pair of positive lenses are disposed downstream a pair of negative lenses for the right and left eyes at the leading end of the scope so as to respectively correspond thereto, whereby aberrations generated by the pair of negative lenses are corrected favorably. Successively from the object side, a negative lens pair 1, a positive lens pair 2, and a positive lens group 3 are disposed, whereby an incident luminous flux from the object side is caused to form an image on an imaging surface 6 of a CCD. The image-surface-side planar surfaces of the lenses $L_2$ in the second lens pair 2 are respectively formed with stops 5 which are attached thereto or deposited thereon. Each of the lenses $L_1$ constituting the first lens pair 1 and its corresponding lens $L_2$ constituting the second lens pair 2, with the stop 5, are integrated together in a concentric state; and thus formed pair of members are disposed in parallel for the right and left eyes, while being made movable symmetrically to each other in directions (arrowed A directions) with respect to the optical axis of the positive lens group 3.

6 Claims, 4 Drawing Sheets

EXAMPLE 1

EXAMPLE 1

EXAMPLE 2

EXAMPLE 3

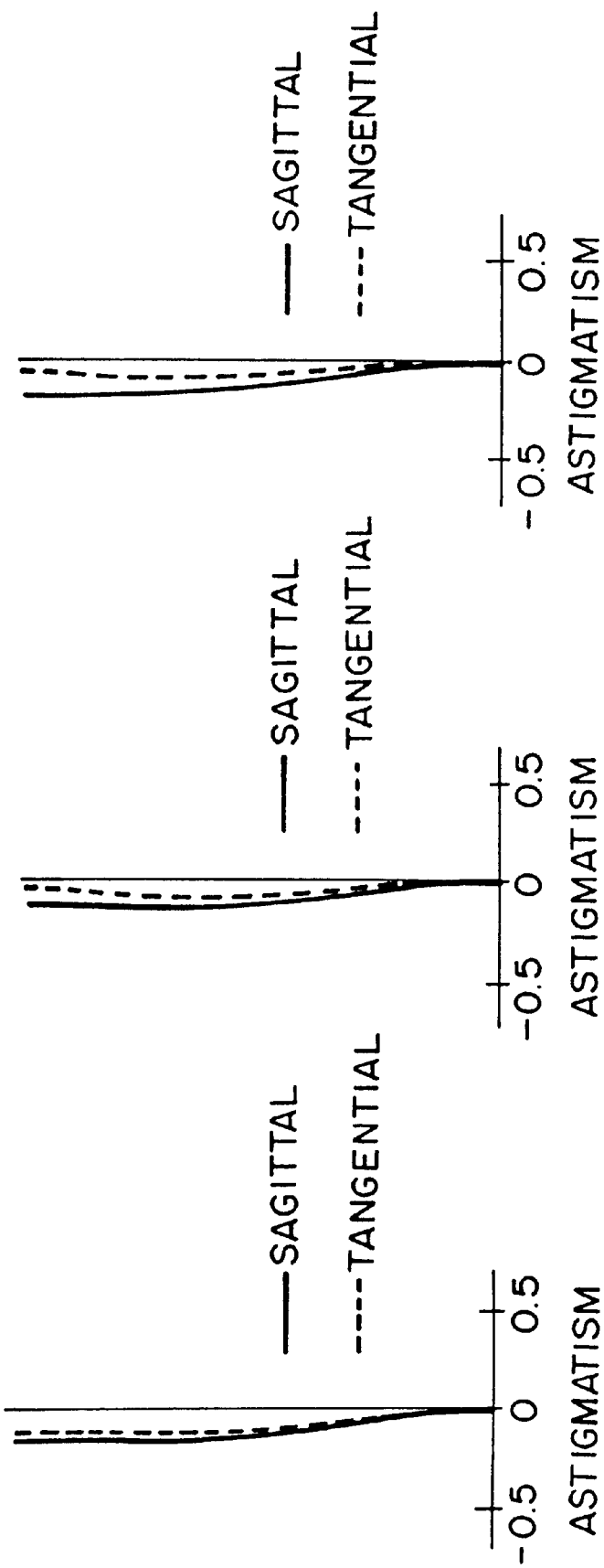
FIG.4A ω=52.7°
FIG.4B ω=56.2°
FIG.4C ω=53.4°

STEREOSCOPIC ENDOSCOPE

RELATED APPLICATIONS

This application is a continuation of Ser. No. 09/066,054, filed Apr. 7, 1998, now U.S. Pat. No. 5,971,915.

This application claims the priority of Japanese Patent Application No. 9-172863 filed on Jun. 13, 1997, which is incorporated herein by reference.

BACKGROUND OF THE INVENTION

1. Field of the Invention

The present invention relates to a stereoscopic endoscope which can stereoscopically observe subject parts such as those inside body cavities and, in particular, to an improvement in configuration of an objective optical system disposed at the tip portion of its inserting portion.

2. Description of the Prior Art

Recently prevailing is a surgical technique in which endoscopes are used for observing subject parts within body cavities and performing operations of affected parts within the body cavities. In order to effect accurate diagnosis and alleviate sufferings of patients, the endoscopes have been technically being improved. In particular, in order to carry out more accurate diagnosis within a body cavity, it is useful to obtain depth information within the body cavity. Stereoscopic endoscopes have been known to respond to such a demand.

Known as such a stereoscopic endoscope is the one disclosed in Japanese Unexamined Patent Publication No. 8-122665, for example.

The endoscope objective optical system disposed at the scope tip of the stereoscopic endoscope disclosed in this publication comprises, successively from the object side, a pair of negative lenses disposed in parallel to each other, and a group of concentric positive lenses. As the number of lens sheets at parts which are separated into right and left sides is reduced, error between right and left images is minimized. Accordingly, the right and left images are easily merged with each other, whereby the fatigue of an observer is alleviated. Also, as a parallel negative lens pair is disposed at the leading end of the scope its positional adjustment is facilitated. Consequently, when assembling the endoscope, an optimal lens position for three-dimensional feel and eccentricity error adjustment of the right and left images can be easily set.

SUMMARY OF THE INVENTION

However, since the lens system at the leading end of the scope is constituted by a pair of negative lenses, and the positive lens group disposed downstream thereof commonly corrects aberrations of both luminous fluxes from the pair of negative lenses in the technique of the above-mentioned publication, it is not always satisfactory in terms of correction of astigmatism and image surface curvature.

In view of such circumstances, it is an object of the present invention to provide a stereoscopic endoscope which, in a simple configuration, can attain a highly accurate three-dimensional image in which aberration is corrected.

Also, there is a strong demand for minimizing relative deviation between the right and left images, which is a problem in stereoscopic endoscopes, such that the right and left images are easily merged with each other, thereby alleviating the fatigue of users. To this aim, it is necessary to enhance accuracy in positional setting of each of members disposed in the lens systems. Operations for actually aligning these members are complicated and likely to generate errors, however. Therefore, it has been required to minimize the number of members necessitating adjustment and facilitate their adjustment.

Further, while it is important for a stereoscopic endoscope to attain an image with a strong three-dimensional feel, a problem not to overlook is the fatigue of a user who continuously uses this stereoscopic endoscope for a long period of time in the case of an actual surgical operation. At the site of actual operation, information with a strong three-dimensional feel is not always necessary continuously from beginning to end. Instead, it is often the case that, after the state is accurately grasped, treatment can be effected while observing an image with a less three-dimensional feel.

It is another object of the present invention to provide an endoscope objective optical system which minimizes errors in right and left images or allows its user to adjust a three-dimensional feel, thereby alleviating the fatigue of the user caused upon image merging.

The present invention provides a stereoscopic endoscope comprising an elongated inserting portion; an objective optical system disposed within a tip of the inserting portion; and imaging means, disposed within the inserting portion, for capturing an object image formed by the objective optical system;

wherein the objective optical system comprises, successively from the object side, a first lens pair made of a pair of negative lenses disposed in parallel to each other, a second lens pair made of a pair of positive lenses disposed in parallel so as to respectively correspond to the lenses of the first lens pair, and a positive lens group.

Preferably, the lenses in the second lens pair in the objective optical system are concentric with their corresponding lenses in the first lens pair.

A stop or light-shielding plate may be disposed between the second lens pair and the positive lens group, while this stop or light-shielding plate, each lens constituting the first lens pair, and its corresponding lens constituting the second lens pair may be integrally formed as a half of a pair of members disposed in parallel.

Preferably, the pair of positive lenses constituting the second lens pair are movable symmetrically to each other in directions perpendicular to the optical axis of the positive lens group.

BRIEF DESCRIPTION OF THE DRAWINGS

FIG. 4A is an astigmatism chart of the objective optical system in the stereoscopic endoscope in accordance with Example 1 of the present invention;

FIG. 4B is an astigmatism chart of the objective optical system in the stereoscopic endoscope in accordance with Example 2 of the present invention; and FIG. 4C is an astigmatism chart of the objective optical system in the stereoscopic endoscope in accordance with Example 3 of the present invention.

DESCRIPTION OF THE PREFERRED EMBODIMENTS

In the following, an embodiment of the present invention will be explained with reference to the drawings.

The stereoscopic endoscope in accordance with the embodiment of the present invention is applied to a so-called electronic endoscope apparatus which has a solid-state imaging device (CCD) at the tip part of the inserting portion of the endoscope.

Namely, in this electronic endoscope apparatus, a luminous flux carrying information of a subject incident on the objective optical system from the tip side of the elongated inserting portion, which can be inserted into a body cavity or the like, forms an image on the CCD. After the image signal data captured by the CCD are transmitted to a control unit connected to an operating section, an image of the subject is displayed on a monitor. On the monitor, an image for the right eye and an image for the left eye having a parallax therebetween are alternately displayed. By observing color images through shutter glasses, the observer can stereoscopically see the subject image. The inserting portion is equipped with an illumination light transmitting means for supplying illumination light from a light source apparatus, and an illumination optical system for emitting the transmitted illumination light through an illumination window so as to illuminate the subject.

In the following, Examples 1 to 3 will be explained with reference to specific data.

EXAMPLE 1

Figure 1:
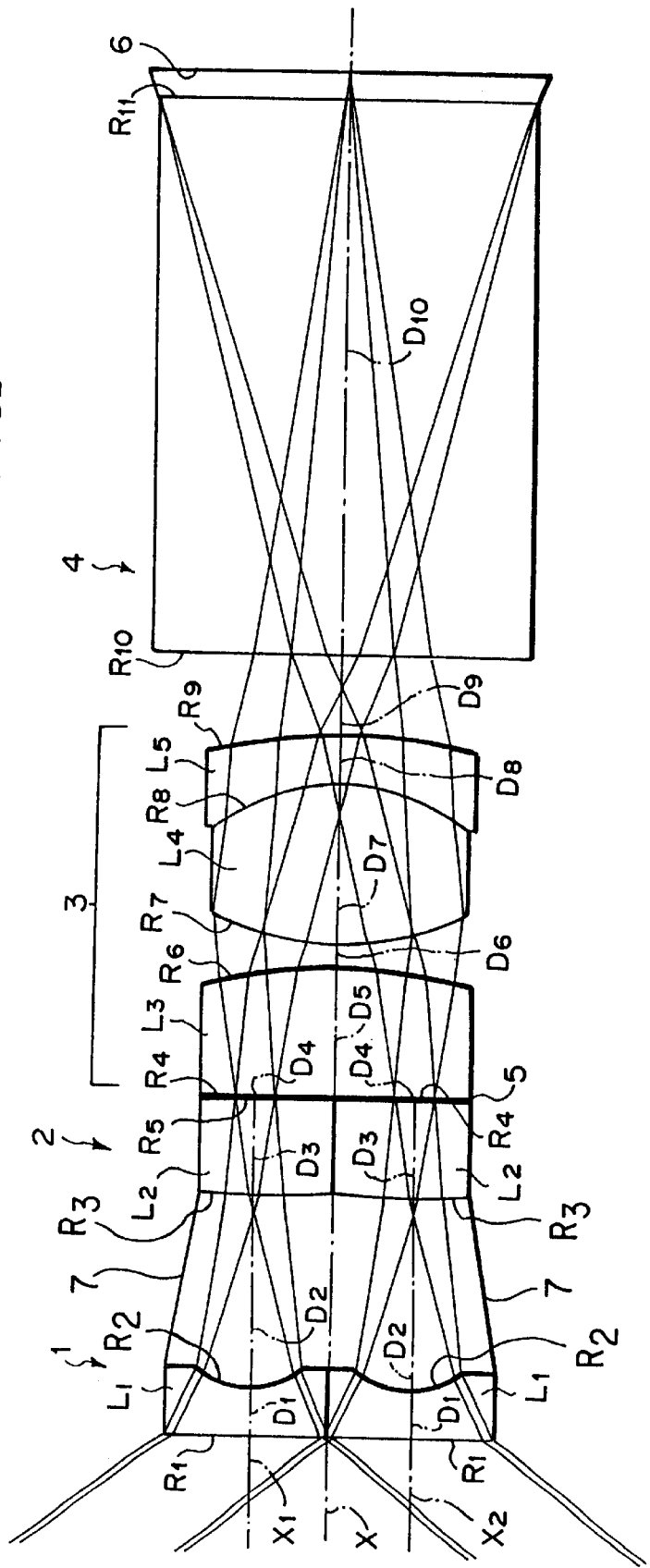
FIG. 1 is a lens configurational view showing the objective optical system in the stereoscopic endoscope in accordance with Example 1 of the present invention.

FIG. 1 is a view showing the configuration of the objective optical system of the stereoscopic endoscope in accordance with Example 1. As depicted, this objective optical system comprises, successively from the object side, a first lens pair 1 in which a pair of negative lenses $L_1$ for the right and left eyes are disposed in parallel to each other; a second lens pair 2 in which a pair of positive lenses $L_2$ for the right and left eyes, concentric with their corresponding lenses in the first lens pair 1, are disposed in parallel to each other; and a positive lens group 3 composed of three sheets of concentric lenses $L_3$, $L_4$, and $L_5$. The objective optical system is configured such that a luminous flux incident thereon from the object side forms an image on an imaging surface 6 of the CCD.

Each of the negative lenses $L_1$ constituting the first lens pair 1 is a planoconcave lens having a concave surface directed onto the image surface side. Each of the positive lenses $L_2$ constituting the second lens pair 2 is a planoconvex lens having a convex surface directed onto the object side. In the lenses constituting the positive lens group 3, the is a planoconvex lens having a convex surface directed onto the image surface side, the lens $L_4$ is a biconvex lens having a surface with a larger curvature directed onto the image surface side, and the lens $L_5$ is a negative meniscus lens having a convex surface directed onto the image surface side. The lenses $L_4$ and $L_5$ in the third lens pair 2 are constituted as a cemented lens. The image-surface-side planar surfaces of the lenses $L_2$ in the second lens pair 2 are respectively formed with stops 5 which are attached thereto or deposited thereon. Each of the lenses $L_1$ constituting the first lens pair 1 and its corresponding lens $L_2$ constituting the second lens pair 2, with the stop 5, are integrated together in a concentric state; and thus form a pair of members disposed in parallel. A filter portion 4 including a low-pass filter and an infrared-cut filter is disposed on the image surface side of the positive lens group 3. Here, the amount of eccentricity of each of the lenses $L_1$ in the first lens pair 1 and the lenses $L_2$ in the second lens pair 2 with respect to the positive lens group 3 is 0.654f (f being the focal length).

Table 1 (follows) shows radius of curvature R of each lens surface, axial surface spacing of each lens (center thickness of each lens and air gap between neighboring lenses) D, and refractive index $n_d$ and Abbe number $v_d$ of each lens at d-line. In Table 1, as well as in the following other tables, numbers referring to each kind of letters successively increase from the object side, whereas the values of R and D are standardized at a focal length of 1 mm. In Table 1, as well as in the following other tables, $D_1$ to $D_4$ are distances on the common optical axes $X_1$ and $X_2$ of the first lens pair 1 and second lens pair 2, whereas $D_5$ to $D_{10}$ are distances on the optical axis X of the positive lens group 3 (as with the following examples).

Of the light from the subject part, a light component transmitted through one of the lenses $L_1$ forming the first lens pair 1 passes through the corresponding one of the lenses $L_2$ forming the second lens pair 2, whereby its aberration caused by the first lens $L_1$ is corrected. Then, this light component is made incident on the positive lens group 3 through the aperture portion of the stop 5, and is converged so as to form an image onto the CCD imaging surface 6 through the filter portion 4.

When one second lens $L_2$ is made to correspond to one first lens $L_1$, the aberration caused by the first lens $L_1$ can be corrected more effectively than in the case where a single second lens is commonly used for correcting aberrations of two lenses constituting the first lens pair 1.

Also, as the corresponding first lens $L_1$ and second lens $L_2$ are disposed concentrically with each other, the endoscope can be made easily. This is because, for example, it is sufficient for spherically symmetrical lenses to be ground at the manufacturing process.

As mentioned above, when the lens $L_1$ of the first lens pair 1, the lens $L_2$ of the second lens pair 2, and the stop 5 are integrally formed as indicated by connection 7, alignment adjustment in the assembling process is facilitated. The resulting improvement in alignment accuracy contributes to reducing errors in the right and left images, thereby alleviating the fatigue of the user.

Further, as the stop 5 is formed on the image-surface-side planar surface of the lens $L_2$ in the second lens pair 2 as being attached thereto or deposited thereon, no member for holding the stop 5 is necessary.

EXAMPLE 2

Figure 2:
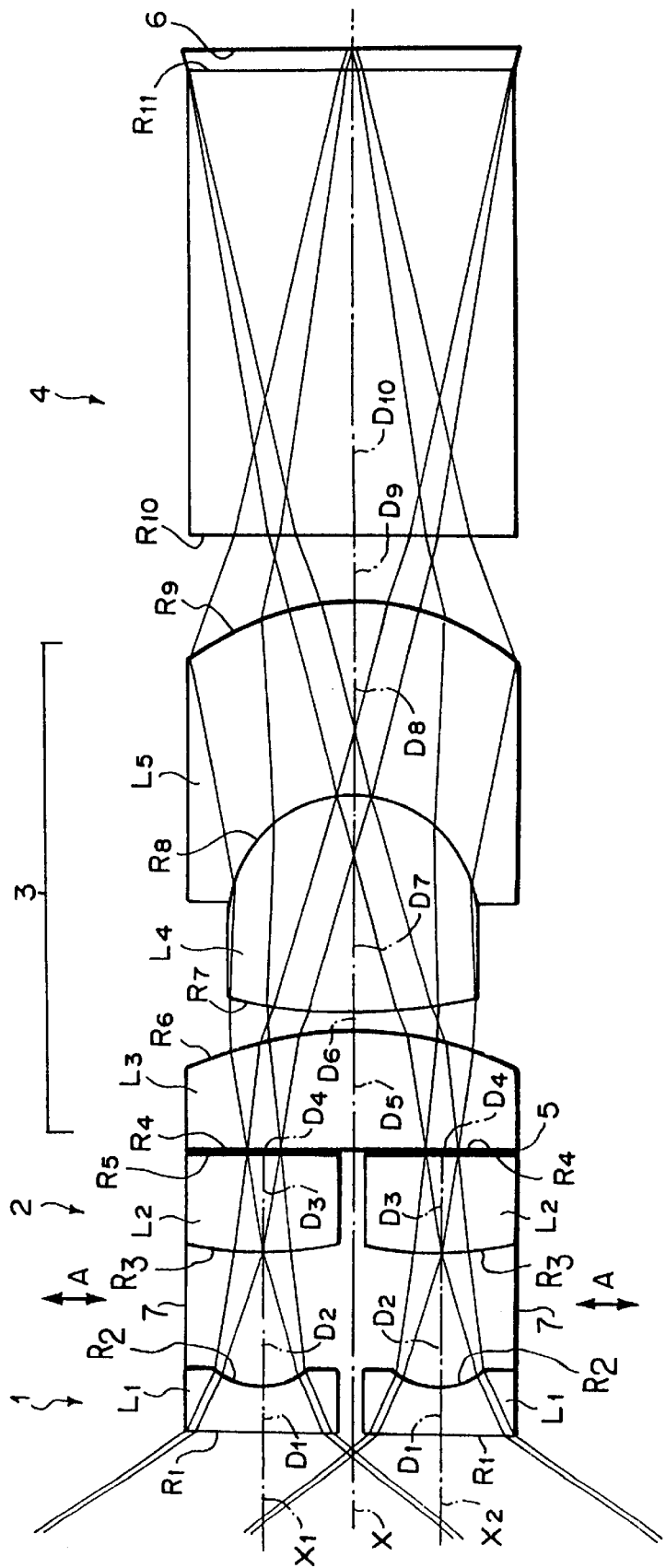
FIG. 2 is a lens configurational view showing the objective optical system in the stereoscopic endoscope in accordance with Example 2 of the present invention.

FIG. 2 is a view showing the configuration of the objective optical system in the stereoscopic endoscope in accordance with Example 2.

As depicted, this objective optical system has a lens configuration substantially similar to that of Example 1 but differs therefrom in that front-stage lens systems each integrally formed with one of e lenses $L_1$ constituting the first lens pair 1, its corresponding lens $L_2$ constituting the second lens pair 2, and the stop 5 attached to or deposited on the second lens pair 2 are movable symmetrically to each other in directions (arrowed directions A in FIG. 2) perpendicular to the optical axis of the positive lens group 3. Here, the amount of eccentricity each of the lenses $L_1$ in the first lens pair 1 and the lenses $L_2$ in the second lens pair with respect to the positive lens group 3 is 0.864f (f being the focal length).

Table 2 (follows) shows radius of curvature R of each lens surface, axial surface spacing of each lens (center thickness of each lens and air gap between neighboring lenses) D, and refractive index $n_d$ and Abbe number $v_d$ of each lens at d-line.

As with Example 1, Example 2 makes it possible to correct aberration and improve accuracy in alignment. In addition, since the front-stage lens systems are movable symmetrically to each other in direct ions perpendicular to the optical axis of the positive lens group 3, the user of the endoscope can adjust angle of introversion, thus being capable of regulating three-dimensional feel when necessary. As a result, the fatigue caused by image merging in the case where the endoscope is used for a long period of time can be alleviated.

EXAMPLE 3

Figure 3:
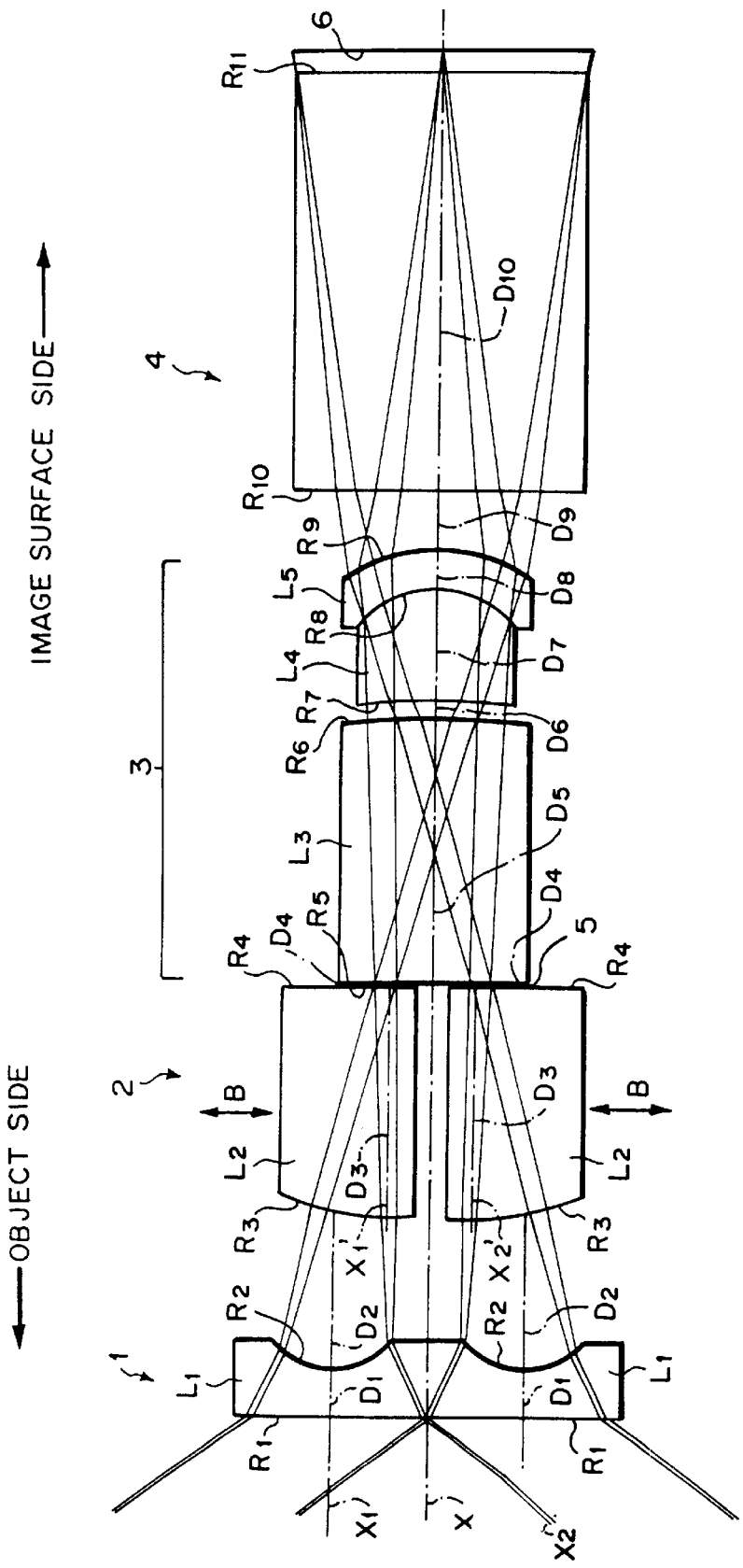
FIG. 3 is a lens configurational view showing the objective optical system in the stereoscopic endoscope in accordance with Example 3 of the present invention.

FIG. 3 is a view showing e configuration of the objective optical system in the stereoscopic endoscope in accordance with Example 3.

As depicted, this objective optical system has a lens configuration substantially similar to that of Example 2 but differs therefrom in that, though the respective lenses $L_1$ and $L_2$ constituting the first lens pair 1 and second lens pair 2 are disposed so as to correspond to each other, they are to concentric with each other. Also, Example 3 differs from Example 2 in that the lenses $L_3$ and $L_4$ constituting the positive lens group 3 are respectively a planoconvex lens having a convex surface directed onto the image surface side and a positive meniscus lens having a convex surface directed onto the image surface side, and that the stop 5 is separately disposed downstream the second lens pair 2. Unlike Example 2 in which each front-stage lens system is concentrically integrated, only the pair of lenses $L_2$ constituting the second lens pair 2 are movable symmetrically to each other in directions (arrowed directions B in FIG. 3) perpendicular to the optical axis X of the positive lens group 3. With respect to the positive lens group 3, the amount of eccentricity of each of the lenses $L_1$ in the first lens pair 1 is 0.924f (f being the focal length), and that of each of the lenses $L_2$ in the second lens pair 2 is 0.455f (f being the focal length).

Table 3 (follows) shows radius of curvature R of each lens surface, axial surface spacing of each lens (center thickness of each lens and air gap between neighboring lenses) D, and refractive index $n_d$ and Abbe number $v_d$ of each lens at d-line.

This example indicates that aberration can be corrected when one lens $L_2$ is made to correspond to one lens $L_1$. As a consequence of such a configuration, no operation is necessary for aligning the lens $L_1$ in the first lens pair 1 and the lens $L_2$ in the second lens pair 2 with each other.

Also, when the pair of lenses $L_2$ constituting the second lens pair 2 are made movable symmetrically to each other in directions perpendicular to the optical axis of the positive lens group 3, the user of e endoscope can adjust angle of introversion, so as to regulate three-dimensional feel when necessary, thus being able to alleviate fatigue. In this case, since only a pair of lenses $L_2$ in the second lens pair 2 are moved, only a small amount of power is required for the movement.

Though the stop 5 is separately disposed downstream the second lens pair 2 in this example, it may be formed as being attached to or deposited on the lenses $L_3$ of the positive lens group 3 from the viewpoint of accuracy in alignment.

FIGS. 4A, 4B, and 4C show astigmatism charts of the lens systems in accordance with Examples 1 to 3, respectively. From these astigmatism charts, it can be seen that each lens in the examples is favorable in terms of aberration.

As explained in the foregoing, in the stereoscopic endoscope in accordance with the present invention, since the lenses in the second lens pair are made to correspond to the lenses in the first lens pair, the aberrations generated by the first lens pair, such as astigmatism and image surface curvature in particular, are corrected, whereby a highly accurate three-dimensional image be obtained in a simple configuration.

When the respective lens 5 in the first and second lens pairs corresponding to each other are disposed concentrically grinding the lenses in the manufacturing process, for example, can be facilitated, thus making it easy to manufacture the endoscope.

When each lens in the first lens pair, its corresponding lens in the second lens pair, and the stop are integrated together, accuracy in alignment can be improved upon assembling the endoscope. Consequently, errors in the right and left images are reduced, thus making it easy to merge the images to yield a three-dimensional image, whereby the fatigue of the user can be alleviated.

In the case where a pair of lenses constituting the second lens pair or front-stage lens systems including the second lens pair are made movable symmetrically to each other in directions perpendicular to the optical axis of the positive lens group, the user of the endoscope can adjust angle of introversion when necessary, thus being able to alleviate the fatigue when using the endoscope for a long period of time.

TABLE 1

| | R | D | $n_d$ | $v_d$ |
|---|---|---|---|---|
| 1 | ∞ | 0.384 | 1.8830 | 40.9 |
| 2 | 0.641 | 1.603 | | |
| 3 | 10.093 | 0.769 | 1.8052 | 25.4 |
| 4 | ∞ | 0.038 | | |
| 5 | ∞ | 1.071 | 1.7130 | 53.9 |
| 6 | −4.489 | 0.192 | | |
| 7 | 2.274 | 1.279 | 1.6204 | 60.3 |
| 8 | −1.757 | 0.384 | 1.8052 | 25.4 |
| 9 | −5.128 | 0.672 | | |
| 10 | ∞ | 4.511 | 1.5163 | 64.1 |
| 11 | ∞ | | | |

TABLE 2

| | R | D | $n_d$ | $v_d$ |
|---|---|---|---|---|
| 1 | ∞ | 0.430 | 1.8830 | 40.9 |
| 2 | 0.623 | 1.326 | | |
| 3 | 3.735 | 0.943 | 1.8052 | 25.4 |
| 4 | ∞ | 0.037 | | |
| 5 | ∞ | 1.118 | 1.7130 | 53.9 |
| 6 | −3.844 | 0.187 | | |
| 7 | 6.081 | 2.060 | 1.6204 | 60.3 |
| 8 | −1.221 | 1.868 | 1.8052 | 25.4 |
| 9 | −2.446 | 0.654 | | |
| 10 | ∞ | 4.389 | 1.5163 | 64.1 |
| 11 | ∞ | | | |

TABLE 3

| | R | D | $n_d$ | $v_d$ |
|---|---|---|---|---|
| 1 | ∞ | 0.461 | 1.8830 | 40.9 |
| 2 | 0.787 | 1.427 | | |
| 3 | 2.237 | 2.219 | 1.8052 | 25.4 |
| 4 | ∞ | 0.042 | | |
| 5 | ∞ | 2.556 | 1.7130 | 53.9 |
| 6 | −6.970 | 0.167 | | |

TABLE 3-continued

|    | R      | D     | $n_d$  | $v_d$ |
|----|--------|-------|--------|-------|
| 7  | −7.654 | 1.087 | 1.6204 | 60.3  |
| 8  | −0.913 | 0.337 | 1.8052 | 25.4  |
| 9  | −1.516 | 0.589 |        |       |
| 10 | ∞      | 3.958 | 1.5163 | 64.1  |
| 11 | ∞      |       |        |       |

What is claimed is:

1. A stereoscopic endoscope comprising:

an elongated inserting portion;

an objective optical system disposed within a tip of said inserting portion; and imaging means, disposed immediately downstream of said objective optical system within said inserting portion, for capturing an object image formed by said objective optical system;

wherein said objective optical system comprises, successively from the object side, a first lens pair made of a pair of negative lenses dispose in parallel to each other, a second lens pair made of a pair of positive lenses disposed in parallel so as to respectively correspond to the lenses of said first lens pair, and a single positive lens group.

2. A stereoscopic endoscope according to claim 1, wherein a stop or light-shielding plate is disposed between said second lens pair and said positive lens group; and wherein said stop or light-shielding plate, each lens constituting said first lens pair, and its corresponding lens constituting said second lens pair are integrally formed as a half of a pair of members disposed in parallel.

3. A stereoscopic endoscope according to claim 1, wherein said pair of positive lenses constituting said second lens pair are movable symmetrically to each other in directions perpendicular to an optical axis of said positive lens group.

4. A stereoscopic endoscope comprising:

an elongated inserting portion;

an objective optical system disposed within a tip of said inserting portion; and imaging means, disposed immediately downstream of said objective optical system within said inserting portion, for capturing an object image formed by said objective optical system;

wherein said objective optical system comprises, successively from the object side, a first lens pair made of a pair of negative lenses disposed in parallel to each other, a second lens pair made of a pair of positive lenses disposed in parallel to each other concentrically with their respective lenses of said first lens pair, and a single positive lens group.

5. A stereoscopic endoscope according to claim 4, wherein a stop or light-shielding plate is disposed between said second lens pair and said positive lens group; and wherein said stop or light-shielding plate, each lens constituting said first lens pair, and its corresponding lens constituting said second lens pair are integrally formed as a half of a pair of members disposed in parallel.

6. A stereoscopic endoscope according to claim 4, wherein said pair of positive lenses constituting said second lens pair are movable symmetrically to each other in directions perpendicular to an optical axis of said positive lens group.

* * * * *

UNITED STATES PATENT AND TRADEMARK OFFICE
CERTIFICATE OF CORRECTION

PATENT NO. : 6,383,131 B1  Page 1 of 1
DATED : May 7, 2002
INVENTOR(S) : Chikara Yamamoto and Hitoshi Miyano It is certified that error appears in the above-identified patent and that said Letters Patent is hereby corrected as shown below:

Column 7,
Line 22, delete the word "dispose" and substitute therefore -- disposed --.

Signed and Sealed this

Second Day of July, 2002

Attest:

JAMES E. ROGAN
Attesting Officer  Director of the United States Patent and Trademark Office